United States Patent [19]

Verduijn et al.

[11] Patent Number: 6,042,808

[45] Date of Patent: Mar. 28, 2000

[54] ZEOLITES AND PROCESSES FOR THEIR MANUFACTURE

[75] Inventors: Johannes Petrus Verduijn, Leefdaal; Machteld M Mertens, Muizen; Marc H Anthonis, Hofstade, all of Belgium

[73] Assignee: Exxon Chemical Patents Inc., Houston, Tex.

[21] Appl. No.: 08/809,164

[22] PCT Filed: Jul. 9, 1996

[86] PCT No.: PCT/EP96/03597

§ 371 Date: Jun. 20, 1997

§ 102(e) Date: Jun. 20, 1997

[87] PCT Pub. No.: WO97/03021

PCT Pub. Date: Jan. 30, 1997

[30] Foreign Application Priority Data

Jul. 10, 1995 [EP] European Pat. Off. .............. 95304800

[51] Int. Cl.[7] .................................................. C01B 39/32
[52] U.S. Cl. .................. 423/709; 423/716; 423/DIG. 28; 423/713
[58] Field of Search ........................... 423/DIG. 28, 700, 423/709, 712, 716, 713, 328.2, 330.1, 332, 333

[56] References Cited

U.S. PATENT DOCUMENTS

| | | |
|---|---|---|
| 3,216,789 | 11/1965 | Breck et al. . |
| 3,781,225 | 12/1973 | Schwartz . |
| 3,808,326 | 4/1974 | McDaniel et al. .................... 423/709 |
| 4,166,099 | 8/1979 | McDaniel et al. . |
| 4,177,653 | 12/1979 | Hickson . |
| 4,544,539 | 10/1985 | Wortel ..................... 423/716 |
| 4,919,907 | 4/1990 | Occelli . |
| 5,064,630 | 11/1991 | Verduijn et al. ................... 423/716 |
| 5,242,675 | 9/1993 | Verduijn ................... 423/DIG. 28 |
| 5,318,766 | 6/1994 | Vaughan et al. ...................... 423/700 |
| 5,330,736 | 7/1994 | Wu et al. ............................. 423/709 |

FOREIGN PATENT DOCUMENTS

| | | |
|---|---|---|
| 142 347 | 5/1985 | European Pat. Off. . |
| 142 349 | 5/1985 | European Pat. Off. . |
| 595 465 | 5/1994 | European Pat. Off. . |
| 323 893 | 7/1997 | European Pat. Off. . |
| 93/08125 | 4/1983 | WIPO . |
| 94/05597 | 3/1994 | WIPO . |
| 94/25151 | 11/1994 | WIPO . |
| 96/01683 | 1/1996 | WIPO . |

OTHER PUBLICATIONS

Meng et al., "Synthesis of Ultrafine Zeolite L," Proc. of the 9th Inter. Zeolite Conf. Montreal 1992, vol. 1, pp. 297–304, 1993.

Xu et al., "Mechanism of Formation and Crystal Growth of Molecular Sieve Zeolite (V). Kinetics of Crystal Growth of L–type Zeolite," Chem,. Ab. vol. 98, p. 622, ab. No. 98:17047u, 1983.

*Primary Examiner*—Mark L. Bell
*Assistant Examiner*—David Sample
*Attorney, Agent, or Firm*—Edward F. Sherer

[57] ABSTRACT

Low temperature hydrothermal treatment of an LTL zeolite-producing mixture produces a colloidal suspension of the zeolite; the suspension may be used as seeds in Al— and Ga—LTL zeolite manufacture.

17 Claims, 13 Drawing Sheets

104,000 ✻

DUPLICATION U.S. 3216789

AVERAGE PARTICLE SIZE
~ 125 nm

CYLINDRICAL KL SYNTHESIZED IN THE PRESENCE OF ppm QUANTITIES OF COLLOIDAL KL AS SEED
FIG. 3    X 10,000*
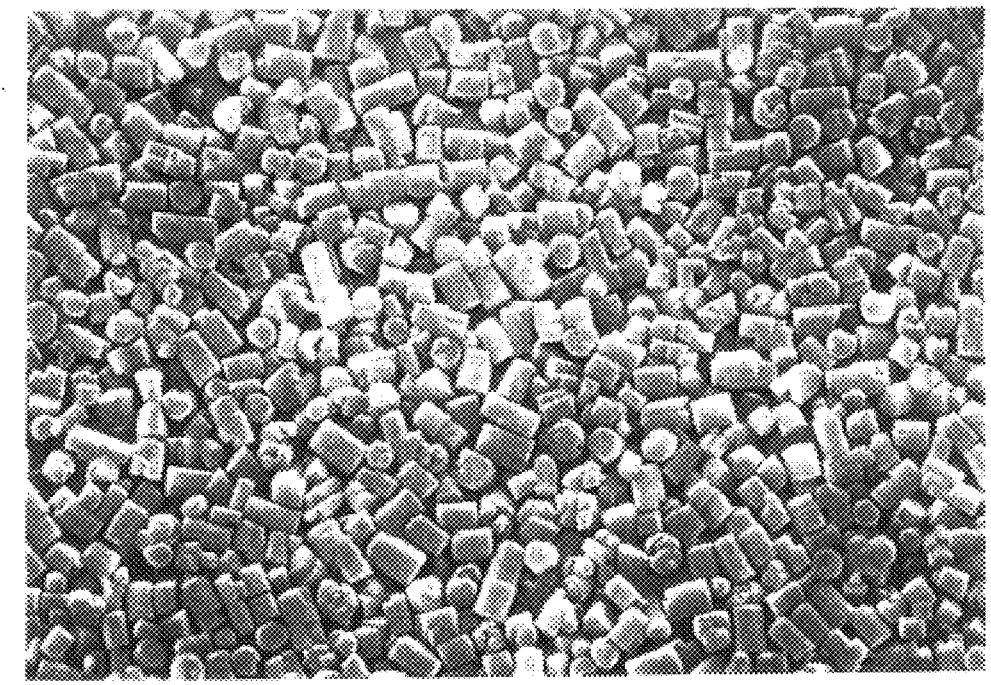
FIG. 4    X 40,000*
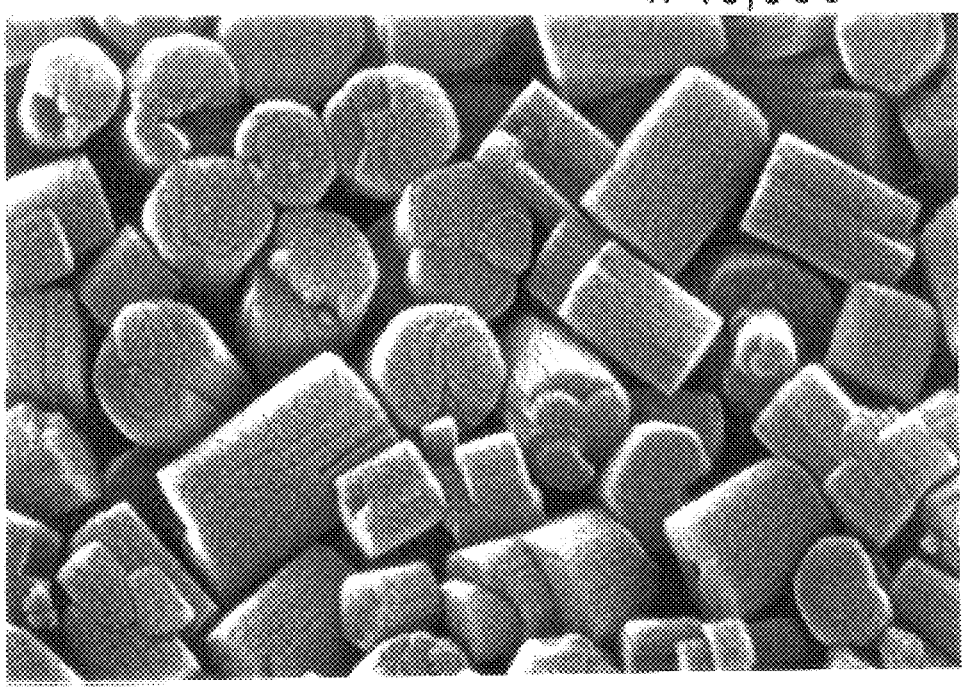

HOCKEY PUCK TYPE KL SYNTHESIZED IN THE PRESENCE OF ppm QUANTITIES OF COLLOIDAL KL AS SEED
FIG. 5        X 10,000*
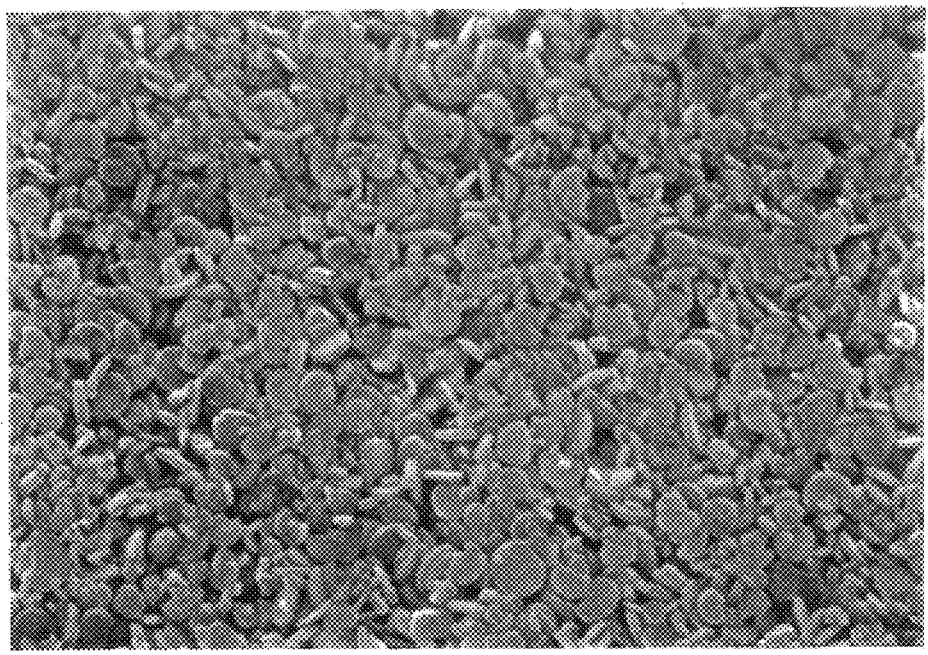
FIG. 6        X 40,000*
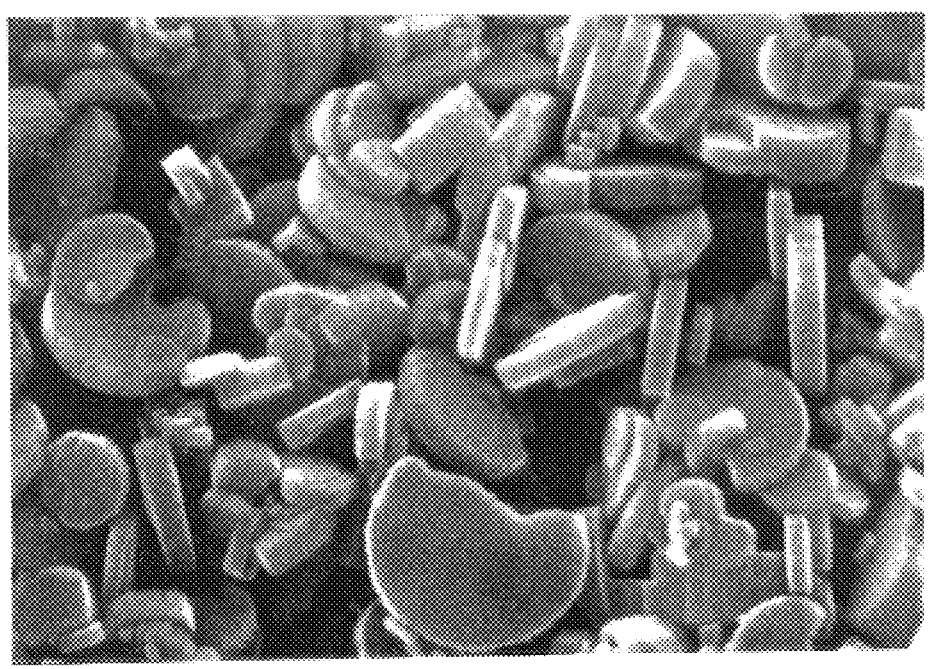

FIG. 8     x 10,000*
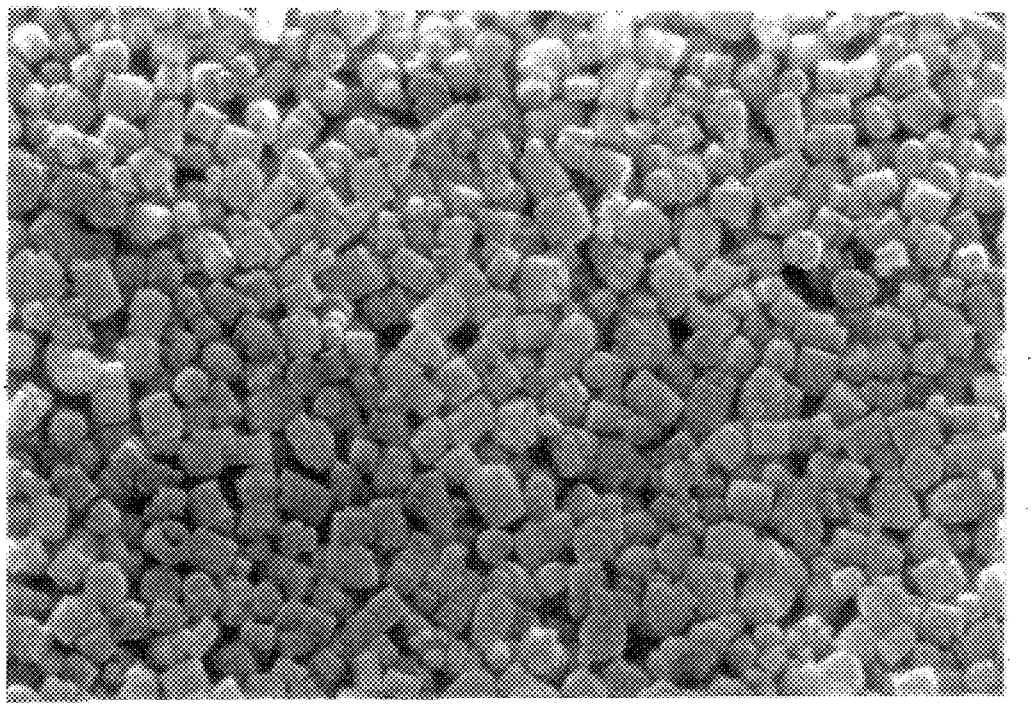
FIG. 9     x 40,000*
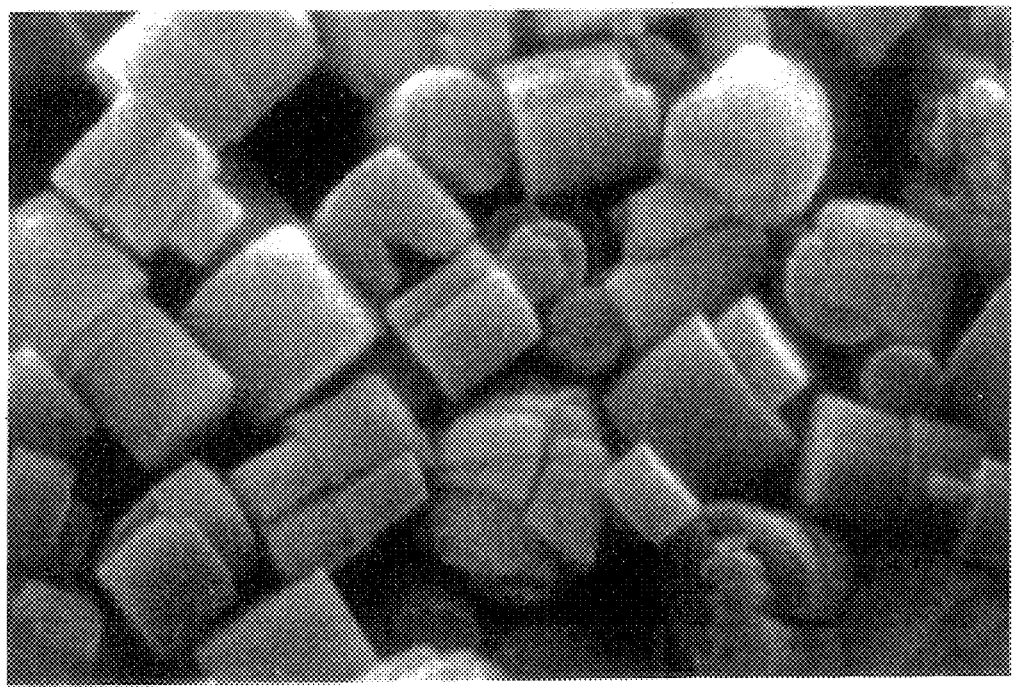

Ga-LTL PRODUCTS OF EXPERIMENTS 1 & 2

EX.1 Ga-LTL SYNTHESIZED WITH 50 wt ppm $Mg^{2+}$     X 10,000*

EX.2 Ga-LTL SYNTHESIZED WITHOUT $Mg^{2+}$ OR SEEDS     X 10,000*

Ga-LTL PRODUCTS OF EXPERIMENTS 3 & 4

EX.3 Ga-LTL SYNTHESIZED WITH 50 wt ppm COLLOIDAL LTL SEEDS

X 10,000*

EX.4 Ga-LTL SYNTHESIZED WITH 250 wt ppm COLLOIDAL LTL SEEDS

X 10,000*

FIG. 14 Ga-LTL PRODUCTS OBTAINED IN EXPERIMENT 5 150°C SYNTHESIS

FIG.15 Ga-LTL PRODUCTS OBTAINED IN EXPERIMENT 5 175°C SYNTHESIS

Ga-LTL PRODUCTS OF EXPERIMENT 5

150°C SYNTHESIS     X 40,000*

175°C SYNTHESIS     X 40,000*

ZEOLITES AND PROCESSES FOR THEIR MANUFACTURE

This invention relates to zeolites of structure type LTL, to processes for the manufacture of such zeolites, and to the use of the zeolites as catalysts and catalyst bases. The zeolites have a 12 membered ring structure with pore dimensions of 0.55 to 0.72 nm.

BACKGROUND OF THE INVENTION

An example of a zeolite of LTL structure type is zeolite L, and processes for the manufacture of zeolite L are described in U.S. Pat. No. 3,216,789, EP-A-219354, and EP-A-595465, the disclosures of all of which are incorporated by reference herein. The two European patent applications, which have extensive prior art discussions to which the reader is referred for more background, and the U.S. Patent list the significant X-ray diffraction data for crystalline zeolite L and give its formula in terms of moles of oxides as $$0.9 \text{ to } 1.3 \text{ M}_{2/n}\text{O:Al}_2\text{O}_3\text{:}5.2 \text{ to } 6.9 \text{ SiO}_2\text{:yH}_2\text{O},$$

where M represents an exchangeable cation of valence n, and y represents a value within the range of from 0 to about 9. In Proceedings of the 9th International Zeolite Conference, Ed. von Ballmoos et al, 1993, p. 297, Xianping Meng et al describe the effect of varying crystallization conditions and reactant ratios on a process for the manufacture of ultrafine (particle size about 30 nm) zeolite L.

Products of such a small particle size have advantages over larger particle size products, such as those produced by the procedure of U.S. Pat. No. 3,216,789, when used as a catalyst, or catalyst base, for reactions involving hydrocarbon conversions because of their enhanced ratio of surface area to mass, high diffusion rates and reactivities, and resistance to deactivation by pore plugging and surface contamination. For similar reasons they have advantages in hydrocarbon separations, and are also valuable as starting materials in the manufacture of supported zeolite layers, especially membranes, as described in WO 94/25151, the disclosure of which is also incorporated herein by reference. For the latter purpose, a zeolite having a particle size, whether in the form of agglomerates or single crystals, of at most 100 nm, and advantageously at most 75 nm, is normally required since the zeolite layer is formed by deposition from a colloidal suspension onto a support; if for any reason the suspension is not stable it is unsuitable for the purpose. Although EP-A-595465 describes the product of the inventive process, in which ammonia is used as a co-solvent to water in the zeolite synthesis mixture, as being in mono-crystalline form, and refers to carrying out the hydrothermal treatment at a temperature in the range of 70 to 160° C. to yield a product having crystallites of diameter less than about 30 nm, it appears from the description and micrograph in the Application that the product consists of larger agglomerates of the nanocrystals incapable of forming a colloidal suspension. The same is true of the product of EP-A-323893, the small crystallites of which agglomerate into readily recoverable particles (page 2, lines 31 to 33).

It has now surprisingly been found that if a synthesis mixture as described in U.S. Pat. No. 3,216,789 is subjected to heat treatment at a temperature below 100° C. a colloidal suspension of zeolite results.

DESCRIPTION OF THE INVENTION

The present invention accordingly provides a process for the manufacture of a colloidal suspension of an LTL zeolite, wherein a synthesis mixture having a composition, given in terms of molar proportions with the solid components being calculated in terms of their oxides, in the ranges:

$K_2O\text{:}(K_2+Na_2O)$ from 0.33 to 1:1
$(K_2+Na_2O)\text{:}SiO_2$ from 0.35 to 0.5:1
$SiO_2\text{:}Al_2O_3$ from 10 to 40:1
solvent:$(K_2O+Na_2O)$ from 15 to 25:1 is subjected to thermal treatment at a temperature below 100° C. for a time sufficient to form a colloidal suspension of an LTL zeolite for the solvent.

Advantageously, the $SiO_2/Al_2O_3$ ratio is at least 12:1, and advantageously the ratio is at most 28:1.

Advantageously, the solvent is water, but the presence of a co-solvent, e.g., ammonia, is not excluded, in which case its molar proportion is included in the specified range.

The invention further provides a process for the manufacture of an LTL zeolite of particle size at most 100 nm, wherein the colloidal suspension prepared as described above is washed with water to a pH within the range of 9 to 12, advantageously 10 to 11, and if desired cation exchanged, dried and, if desired, calcined.

Advantageously, the resulting zeolite is one having a composition of Formula I $$0.9 \text{ to } 1.3 \text{ M}_{2/n}\text{O:Al}_2\text{O}_3\text{:}5.2 \text{ to } 6.9 \text{ SiO}_2 \qquad \text{I}$$

wherein M is an exchangeable cation of valence n.

The process of the invention provides either individual crystals or agglomerates which form a colloidal suspension, i.e., the suspension produced directly, or by washing, is a stable one.

A stable suspension is one in which settlement does not take place, or one in which any settlement that takes place does so so slowly as to be insignificant over the relevant timescale. Such a suspension is referred to herein as colloidal.

As described above, the zeolites of the invention are primarily aluminosilicates, and will be described herein as such. It is, however, within the scope of the invention to replace aluminium, wholly or partly, with gallium, and partly with boron, iron or other trivalent elements, and silicon may similarly be replaced by germanium or phosphorus. It is also within the scope of the invention to include cations other than potassium and sodium in the synthesis mixture.

The sources of the various elements required in the final product may be any of those in commercial use or described in the literature, as may the preparation of the synthesis mixture.

For example, the source of silicon may be a silicate, e.g., an alkali metal silicate, or a tetraalkyl orthosilicate, but there is preferably used an aqueous colloidal suspension of silica, for example one sold by E. I. du Pont de Nemours under the trade name Ludox. Ludox HS-40 is a sodium-containing product, while AS-40 contains very little sodium.

The source of aluminium is preferably $Al_2O_3\text{.}3H_2O$, dissolved in alkali. Other aluminium sources include, for example, a water-soluble aluminium salt, e.g., aluminium sulphate, or an alkoxide, e.g., aluminium isopropoxide.

The potassium source is advantageously potassium hydroxide and the sodium source, if present, is advantageously also the hydroxide.

The synthesis mixture is conveniently prepared by mixing two solutions, one containing the potassium and aluminium sources, and the other the silica source, each containing water in a quantity such that, on mixing, the required molar proportions result.

Crystallization is effected, either under static conditions or with moderate stirring, and, if desired, under reflux.

Thermal treatment (also known as ageing at elevated temperature) at a temperature in the range of from 40 to 97° C. is convenient; advantageously from 40 to 95° C. and preferably from 40 to 85° C. Although crystallization times are normally described in the prior art as being longer at lower temperatures, it has been surprisingly found that, while times from 48 to 500 hours may be used, even at temperatures at the lower end of the present range, times up to 84 hours may suffice. A lower temperature in general gives a smaller particle size zeolite, if other conditions remain constant. By appropriate choice of temperature, agglomerates of greatest dimensions in the range of 25 nm to 100 nm may be obtained, with good uniformity of particle sizes.

The synthesis mixture may, if desired, be aged at a temperature below that at which crystallization takes place, i.e., at a temperature less than 40° C., for example for up to 2 days. Including this low temperature ageing generally results in a smaller crystallite size, compared with an otherwise similar procedure omitting it.

The colloidal suspension, or the crystals obtainable from the suspension, produced by the processes described above may be used in a number of applications including the manufacture of thin films on substrates, in which application the crystals may provide a growth-enhancing layer, or as the base of the film itself, for example by multiple in-situ crystallization. More especially, however, according to the present invention, the nanometric sized zeolite L particles may be used as seeds in the manufacture of zeolite L.

As noted in U.S. Pat. No. 3,216,789, if a synthesis mixture has a composition falling outside a certain range it tends to produce a zeolite other than zeolite L, zeolite L contaminated with other zeolites or with amorphous material, or an amorphous product only. For example, too low an alkalinity results in zeolite W formation, or in zeolite L contaminated with zeolite W.

It has previously been proposed, in U.S. Pat. No. 5,330,736, to manufacture zeolite L using as seeding gel an amorphous aluminosilicate seeding gel which does not contain zeolite L. The gel is stated to be one which, if heated to 100° C. on its own would produce zeolite Y. In the patent, a number of earlier U.S. patents are discussed which are stated to mention the possibility of seeding zeolite L-producing synthesis mixtures with zeolite L seeds. Examples 12 and 13 of U.S. Pat. No. 4,657,749, one referred to in Patent No. 5,330,736, describe a seeding process, in which seeds of an unspecified particle size zeolite L are used. In a comparison example in U.S. Pat. No. 5,330,736, a preformed crystalline zeolite L of unspecified particle size was used to seed a zeolite L-forming synthesis mixture, with a zeolite T-contaminated zeolite L product resulting.

It has now been found that colloidal zeolite L seeds may successfully be used to promote the formation of zeolite L from a synthesis mixture, even if that mixture is one which, in the absence of colloidal seeds, would give a product other than pure zeolite L.

In U.S. Pat. No. 5,396,009, there is described a procedure for obtaining zeolite L with a very desirable morphology, one in which crystallites are substantially cylindrical with basal planes so shaped that the ratio of the axial length of curved cylindrical surface to the total length of the crystallite is at least 0.9, and in which the aspect ratio of the length to the diameter is preferably at least 0.5. The crystallites typically have a mean diameter in the region of 0.05 to 0.5 $\mu$m.

The zeolites described in the U.S. Patent are aluminium-based; syntheses of gallium-based zeolites of similar morphology using the same procedure have encountered some difficulties.

It has now been found that the addition of a colloidal suspension of zeolite L seeds to a gallium-containing zeolite L-forming synthesis mixture yields pure crystalline Ga-LTL zeolite having reduced contamination by, for example, Zeolite W, and a controlled morphology and particle size. Advantageously, the Ga-LTL zeolite contains less than 0.2% by weight alumina.

The present invention accordingly provides gallium-containing LTL zeolite formed of cylindrical crystallites having basal planes so shaped that the ratio of axial length of curved cylindrical surface to the overall axial length of the crystallites is greater than 0.9 and the aspect ratio of length to diameter is at most 0.5.

Advantageously the mean length of the crystallites is less than 0.6 $\mu$m and advantageously the mean diameter is less than 1.5 $\mu$m.

Because of the reduced acidity of a Ga-LTL zeolite compared with an Al-LTL zeolite of corresponding molar composition and similar physical characteristics, the Ga-LTL provides advantages when used as a catalyst or catalyst component, e.g., one admixed with a catalyst metal, in several hydrocarbon conversions, e.g., aromatization.

The present invention also provides a process for the manufacture of an LTL zeolite which comprises forming a synthesis mixture having a composition, given in terms of molar proportions with the solid components calculated in terms of their oxides, in the ranges:

| | |
|---|---|
| $K_2O:(K_2O + Na_2O)$ | from 0.60 to 1:1 |
| $(K_2O + Na_2O):SiO_2$ | from 0.18 to 0.36:1 |
| $SiO_2:Al_2O_3$ or $Ga_2O_3$ | from 5 to 18:1 |
| $H_2O:(K_2O + Na_2O)$ | from 25 to 90:1 | and also containing seed crystals of an LTL zeolite of particle size at most 100 nm, and subjecting the seed-containing synthesis mixture to a hydrothermal treatment at a temperature and for a time sufficient to form an LTL zeolite.

Advantageously, when $Al_2O_3$ is used the $SiO_2/Al_2O_3$ ratio is from 5 to 15; when $Ga_2O_3$ is used the ratio is from 5 to 18.

Advantageously, the LTL zeolite is zeolite L.

The crystallites of the resulting LTL zeolite are advantageously in the form of cylinders with basal planes of such a shape that the ratio of axial length of curved cylindrical surface (m) to the overall axial length of the crystallite (h) is greater than 0.9, and preferably approaches 1. (A geometrically perfect cylinder with completely flat basal planes would have m=h, and m/h=1, while any doming or growths on the basal surfaces mean that h is greater than m.)

The cylindrical crystallites advantageously have a mean diameter (d) of at least 0.05 $\mu$m, preferably at least 0.1 $\mu$m. For certain applications of the crystallites, the diameter of the crystallite is advantageously from 0.3 to 1.5 $\mu$m, preferably 0.4 to 1.0 $\mu$m and the length of the crystallite is advantageously from 0.1 to 0.6 $\mu$m, preferably 0.1 $\mu$m to 0.3 $\mu$m. The aspect ratio (the ratio of the axial length of the cylindrical surface m to the mean diameter d) is advantageously less than 2, preferably less than 1 and most preferably 0.8 or less. For certain applications, the crystallites advantageously have a hockey puck shape (aspect ratio 0.2 to 0.5) or coin shape (aspect ratio less than 0.2).

A particularly advantageous LTL zeolite of the invention comprises crystallites in the form of well-defined, smooth-surfaced cylinders with substantially flat basal planes, i.e., they have a m/h ratio of substantially unity. Preferably the LTL zeolite comprises cylindrical crystallites wherein at least 80%, preferably at least 90%, of the basal planes are microscopically flat to within 20 nm, and thus do not exhibit spiral step growths thereon.

The LTL zeolite of the invention is characterized by its cylindrical morphology. The terms "cylinder" and "cylindrical" are used herein to describe the shape of a cylinder as defined in solid geometry, i.e., a solid bounded by a surface generated by a line moving parallel to a fixed line so as to cut a fixed plane curve and by two parallel planes (bases) intersecting the surface. The cylinders will generally be circular cylinders, that is, with circular cross-section, but in the context of the invention the cylinders may also exhibit some flattening of the cylindrical surface such that the cross-section has polygonal, and particularly hexagonal, character—that is to say, is in the form of a curvilinear hexagon—and the terms "cylinder" and "cylindrical" as used herein include such forms.

It has surprisingly been found that the addition in the form of a colloidal suspension of very small proportions of zeolite seeds is effective to promote crystallization of the desired zeolite from the synthesis mixture without contamination with other crystalline zeolite forms or amorphous material. Because of the small proportions of seed crystals necessary, the seed may be aluminium-based zeolite L in the synthesis of Ga-LTL without affecting the substantially gallium-based nature of the resulting product. The resulting particles have a narrow particle size distribution, which is advantageous for the intended uses of the zeolite product. The product of EP-A-142347, which is formed by adding to a synthesis mixture a slurry of seeds of particle size too great to form a colloidal suspension, comprises material with a wide particle size distribution, e.g., about 1 to 3 $\mu$m, and contamination with zeolite W.

In contrast to the above-mentioned comparative example in U.S. Pat. No. 5,330,736, which employed about 0.5% by weight of seeds, based on the total synthesis mixture, the process of the present invention is effective with ppm proportions of colloidal seeds, e.g., from 0.005% to 0.10% by weight, based on the weight of the total synthesis mixture, advantageously from 0.015% to 0.05%, conveniently about 0.025%. Although it is within the scope of the invention to employ a greater proportion, no technical advantage appears to result.

The seeds, prepared conveniently as described above, advantageously have a particle size within the range of from 25 nm to 100 nm, preferably from 60 to 80 nm.

As indicated above, the procedure includes adding the seeds in the form of a colloidal suspension. It is believed that if the colloidal suspension is evaporated to dryness the resulting dried seeds are changed in an adverse way; in any event a product made using dried seeds tends to be contaminated.

Hydrothermal treatment is advantageously carried out at a temperature of 100° C. to 180° C., preferably from 150° C. to 175° C., for a time advantageously within the range of 4 to 200 hours, preferably for from 20 to 80 hours, advantageously under autogenous pressure.

It has surprisingly been found possible to carry out the thermal treatment with stirring. This is surprising because in the normal synthetic methods for preparing zeolite L from a low alkaline synthesis mixture stirring had to be avoided since its use resulted in the undesired formation of Zeolite W. While static conditions are acceptable in small scale operations, on an industrial scale stirring is often required for a commercially viable heating regime. The presence of crystalline nucleating agents, especially the colloidal seeds produced by the first aspect of the present invention, makes it possible to produce zeolite L without contamination by zeolite W in a stirred synthesis mixture.

The thermal treatment may accordingly be carried out under static conditions or with stirring.

The sources of the various components of the synthesis mixture, other than the seeds, may be as described with reference to the first embodiment of the invention, the formation of the colloidal LTL zeolite suspension, while the seeds are advantageously the product of the first embodiment of the invention.

By using the seeding process of the invention, zeolite L formation is promoted in, for example, synthesis mixtures that are prone to yield zeolite T or W product, i.e., the seeds act as a structure-directing agent.

The invention further provides the use, in a process for the hydrothermal treatment of a synthesis mixture for Zeolite L, of a temperature below 100° C. to obtain a colloidal suspension of Zeolite L, or to obtain particles of zeolite L having a greatest dimension of at most 100 nm.

The invention further provides the use, in the hydrothermal treatment of a zeolite-forming synthesis mixture, of a colloidal suspension of seeds of zeolite L, i.e., of seeds having a greatest dimension of at most about 100 nm, to promote the crystallization from the synthesis mixture of a zeolite L-containing product, advantageously a product consisting essentially of zeolite L, and preferably a pure zeolite L product. Increasing the concentration of colloidal zeolite L seeds reduces the product particle size if the conditions are otherwise kept constant.

The zeolite L produced by the second aspect of the invention, if required after washing, cation exchange and/or calcining, is suitable for use as a catalyst in numerous hydrocarbon conversions or is effective in hydrocarbon separations or adsorptions. The zeolite L material may be used, alone or in admixture with other zeolites, in particulate form or in the form of a layer on a support, especially as a membrane. Supported layers may be made by the procedures described in International Application WO 94/25151 and WO 96/01683, the disclosures of which are incorporated herein by reference.

More especially, however, the invention provides a process for the manufacture of a zeolite L-containing structure comprising a substrate and a zeolite L-containing layer, comprising contacting a face of the substrate with a colloidal suspension of zeolite L, i.e., a suspension in which the particle size is at most about 100 nm, to form an intermediate layer, and subsequently forming on the said face a zeolite L-containing layer by crystallization thereon of zeolite L by hydrothermal treatment of a zeolite-forming synthesis mixture. Advantageously the synthesis mixture is a pourable gel when it is contacted with the treated face of the substrate. The face of the substrate may be pretreated with a barrier layer forming material, e.g., water, before forming the intermediate layer thereon. Alternatively, the face of the substrate may be dry when the dispersion of zeolite L is applied.

The invention also provides a structure comprising a substrate, an intermediate layer, and an upper layer, the intermediate layer comprising zeolite L of a particle size of at most 100 nm, the upper layer comprising zeolite L particles, the particles of zeolite in the upper layer having at least one dimension greater than the dimension of the particles of the intermediate layer. Advantageously, the orientation of at least 75% of zeolite L particles is such that the 12-membered ring pores (the c-axis) lie within 30° of the perpendicular to the plane of the layer. Preferably, the orientation of at least 75% of the zeolite L particles in the upper layer is such that the c-axis of the particles lies within 5° of the perpendicular to the plane of the layer.

The LTL zeolite of the present invention may be used as a catalyst base and may be used in combination with a catalytically active metal in a wide variety of hydrocarbon conversion process. Examples of catalytically active metals include Group VIII metals, e.g., platinum and palladium.

A particularly advantageous catalyst composition incorporates from 0.1 to 6.0 wt % (based on the total weight of the composition), preferably from 0.1 to 1.5 wt %, platinum or palladium, since this gives excellent results in aromatization. From 0.4 to 1.2 wt % platinum is particularly preferred. Accordingly the invention provides a catalyst comprising the LTL zeolite produced by the seeding process of the invention and a catalytically-active metal.

There may also be incorporated into the catalyst of the invention as a binder one or more materials substantially inert under the conditions in which the catalyst is to be employed. Such binders may also act to improve the resistance of the catalyst to temperature, pressure and attrition. Examples of suitable binders include synthetic or naturally occurring inorganic materials, e.g., clays and/or metal oxides, for example, silica, alumina, titania, and/or zirconia. Examples of naturally occurring clays include those of the montmorillonite and kaolin families, which families include the sub-bentonites and the kaolins commonly known as Dixie, McNamee, Georgia and Florida clays or others in which the main mineral constituent is halloysite, kaolinite, dickite, nacrite, or anauxite. Such clays may be used in the raw state, as originally mined or be subjected to calcination, acid treatment, or chemical modification. Other matrix materials which find particular application in the present invention include porous matrix materials, e.g., silica-alumina, silica-magnesia, silica-zirconia, silica-thoria, silica-beryllia, and silica-titania, as well as ternary compositions, e.g., silica-alumina-thoria, silica-alumina-zirconia, silica-alumina-magnesia, and silica-magnesia-zirconia. A preferred binder comprises particles of zeolitic materials which materials are disclosed in U.S. Pat. No. 5,486,348 and International Application WO 96/16004, the disclosures of which are incorporated herein by reference.

The LTL zeolite of the present invention may be used in hydrocarbon conversions and has low acidity, advantageous in catalytic applications, e.g., aromatization, where low acid site strength is desired. Hydrocarbon conversions include, for example, cracking, reforming, hydrofining, aromatization, alkylation, transalkylation, dealkylation, dehydrogenation, hydrogenation, dewaxing, hydrodewaxing, alcohol conversion, oligomerization, isomerization and hydrocracking. Of especial importance are hydrocyclization and/or isomerization of aliphatic hydrocarbons in which the hydrocarbons are contacted at a temperature of from 370° C. to 600° C., preferably 430° to 550° C., with a catalyst comprising zeolite L of the invention, preferably having at least 90% of the exchangeable cations M as alkali metal ions, and incorporating at least one Group VIII metal having dehydrogenating activity, e.g., palladium or platinum, so as to convert at least part of the aliphatic hydrocarbons into aromatic hydrocarbons.

The aliphatic hydrocarbons may be straight or branched chain acyclic hydrocarbons, and particularly paraffins, e.g., hexane, although mixtures of hydrocarbons may also be used, e.g., paraffin fractions containing a range of alkanes possibly with minor amounts of other hydrocarbons. Cycloaliphatic hydrocarbons, e.g., methylcyclopentane, may also be used. In a preferred aspect the feed to a process for preparing aromatic hydrocarbons, and particularly benzene, comprises hexanes. The temperature of the catalytic reaction may be from 370° to 600° C., preferably 430° to 550° C. and preferably pressures in excess of atmospheric are used, for example up to 2000 KPa, more preferably 500 to 1000 KPa. Hydrogen is employed in the formation of aromatic hydrocarbons, preferably with a molar ratio of hydrogen to feed of less than 10.

In a further aspect, the present invention provides a method for the dehydrocyclization and/or isomerization of an aliphatic hydrocarbon comprising contacting the hydrocarbon at a temperature in the range of from 370° C. to 600° C. with a catalyst so as to convert at least part of the hydrocarbon into an aromatic hydrocarbon, the catalyst comprising a catalytically active metal and gallium-containing LTL zeolite formed of cylindrical crystallites having basal planes so shaped that the ratio of axial length of curved cylindrical surface to the overall axial length of the crystallite is greater than 0.9.

BRIEF DESCRIPTION OF THE DRAWINGS

FIGS. 3 and 4 are SEM micrographs at 10,000 and 40,000 magnification, respectively, of the product of Example 5.

FIGS. 5 and 6 are SEM micrographs at 10,000 and 40,000 magnification, respectively, of the product of Example 7.

FIGS. 8 and 9 are SEM micrographs at 10,000 and 40,000 magnification, respectively, of the product of Example 8.

The following examples illustrate the invention.

COMPARISON EXAMPLE A

Example 1 of U.S. Pat. No. 3,216,789 was repeated.

The following two solutions were prepared:

| Solution A | parts by weight |
| --- | --- |
| KOH pellets, 87.4% purity (Baker) | 53.17 |
| Al(OH)$_3$, 98.5% purity (Alcoa) | 8.20 |
| H$_2$O, deionized | 57.19 |

The potassium and aluminium sources were mixed with the water which was boiled until a clear solution resulted. After cooling to room temperature, any water loss was corrected.

| Solution B | parts by weight |
|---|---|
| SiO$_2$, Ludox H540, 40% SiO$_2$ by weight | 155.54 |
| H$_2$O, deionized | 23.13 |

Solution A was quantitatively added to Solution B with stirring. The resulting synthesis mixture had a molar composition of 8.0 K$_2$O:Al$_2$O$_3$:20 SiO$_2$:200 H$_2$O A portion of the synthesis mixture was transferred to a glass liner, which was placed in a stainless steel autoclave. The autoclave was placed in an oven, which was then heated from room temperature to 100° C. over a 2 hours period, and maintained at that temperature for 169 hours.

After cooling, the autoclave was opened and the contents of the liner were examined. A product had settled on the bottom leaving a clear mother liquor. The product was washed several times with water to reach a pH of 10.2, and then dried in an oven.

Figure 1:
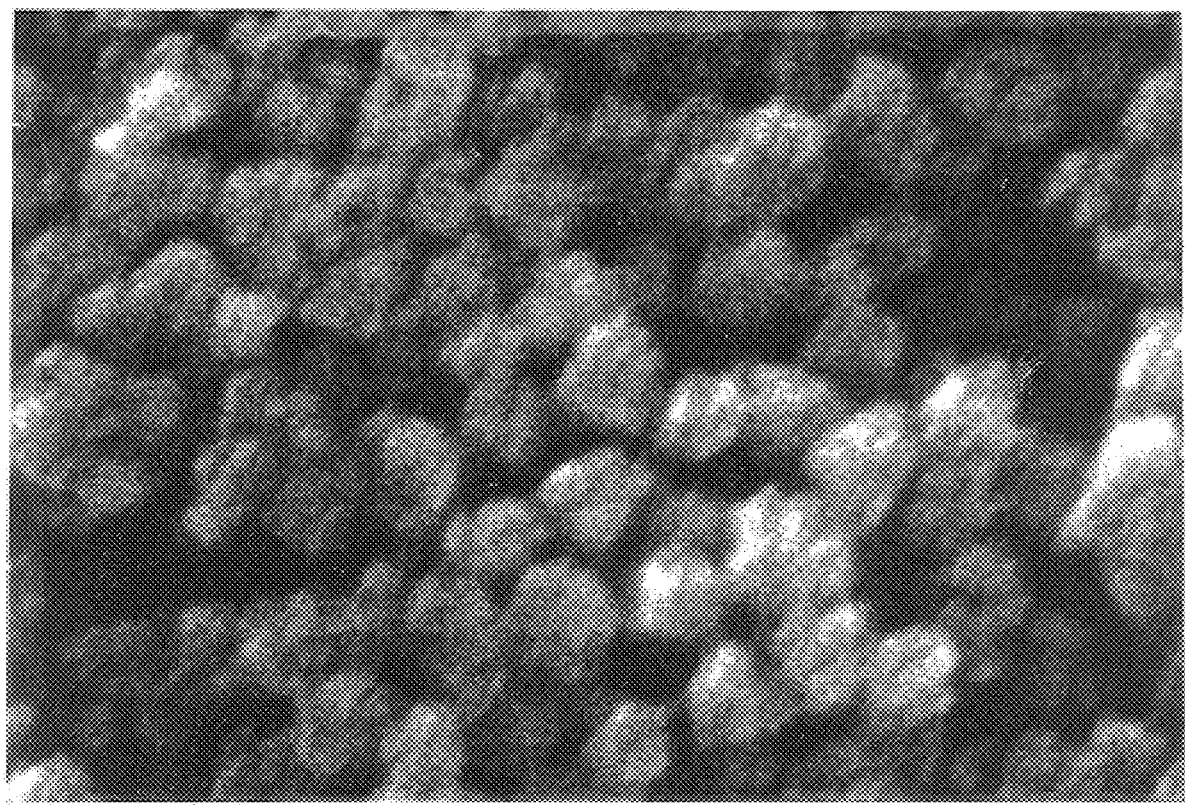
FIG. 1 is a scanning electron microscope (SEM) micrograph of the product of Comparison Example A.

X-ray diffraction (XRD) showed a pattern characteristic of zeolite KL. Scanning electron microscopy (SEM) shows spherical agglomerates with an average size of 125 nm, as shown in FIG. 1.

EXAMPLES 1 to 3

The procedure of Comparison Example A was followed up to the preparation of the synthesis mixture, but various samples of the resulting mixture were thermally treated at the temperatures and for the times shown in Table 1 below. Crystallization was effected in polypropylene vessels under reflux conditions. The resulting reaction mixtures were washed with water to a pH of between 10 and 11, and kept in the last wash water. Separation of the product from the final wash waters was effected by high speed centrifugation. In Example 3, a sample was taken from the reaction mixture after 68 hours heating. A portion of this sample and of each of the washed slurry products of the completed experiments was dried and used to obtain X-ray diffraction and SEM data. The XRD and SEM results show that the product of Example 3 was the same after 68 hours as after the complete 164 hour treatment.

TABLE 1

| | Effect of Crystallization Temperature on SEM particle size | | | Particle |
|---|---|---|---|---|
| Example | Crystallization Temp. °C. | Time, hours | XRD | Size, nm by SEM |
| 1 | 92.5 | 408 | KL - peak broadening | ≈75 |
| 2 | 82.5 | 432 | KL - peak broadening | ≈50 |
| 3a | 72.5 | 68 | KL, extremely weak pattern | ≈30 |
| 3b | 72.5 | 164 | | ≈30 |

Figure 2:
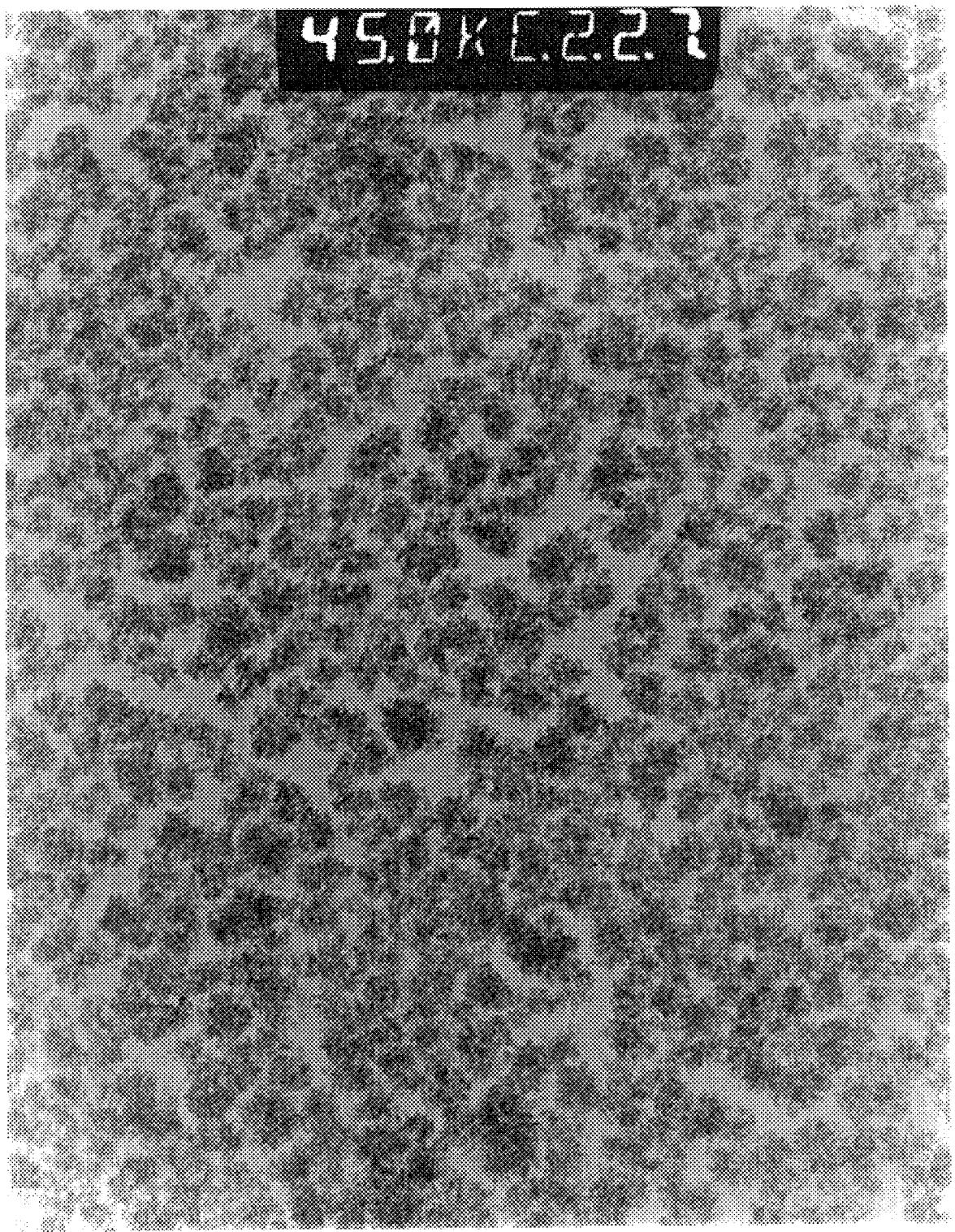
FIG. 2 is a transmission electron microscope (TEM) micrograph of the product of Example 3.

The washed reactor slurries of Example 1 to 3 were transferred to plastics containers and left undisturbed for 7 days. The suspended KL products showed no tendency to settle on the container bases. All Examples 1 to 3 products showed a very weak but still recognizable XRD pattern of KL, with no amorphous halo whose presence would show contamination by amorphous by-products. A TEM micrograph of the Example 3 product is shown in FIG. 2.

The toluene adsorption properties of the products of Examples 1 to 3 were compared with those of a highly crystalline (as shown by XRD) standard KL product. The results are shown in Table 2.

TABLE 2

| | Toluene Capacity, wt % | |
|---|---|---|
| Material | Micropore* | Macropore |
| Standard KL | 9.95 | 0.24 |
| Example 1 | 8.71 | 13.31 |
| Example 2 | 10.65 | 10.10 |
| Example 3 | 10.35 | 10.00 |

*Wt % Toluene absorbed after 60 minutes desorption with N$_2$, 30° C.

The results confirm the crystallinity of the products of Examples 1 to 3. Their increased macropore capacity indicates that there are small voids between individual nanometer-sized KL particles.

EXAMPLE 4

A synthesis mixture with the same molar composition as Comparison Example A and Examples 1 to 3 was aged at 97° C. for 74 hours. The aged product was washed with water, separated from the wash water in a high speed centrifuge, again suspended in water and centrifuged and again suspended in water, the process being repeated until the pH of the washwater reached 10.8.

Inspection of the suspension after overnight standing showed that a very small proportion of the solid content had settled on the bottom of the vessel. XRD of dried solid product showed the characteristic pattern of zeolite L. Scanning and transmission electron microscopy indicated a particle size range of 100 to 110 nm. The example shows that 97° C. is close to the upper limit at which colloidal KL crystals are formed by the procedure according to the invention.

EXAMPLE 5

The following two solutions were prepared:

| Solution A | parts by weight |
|---|---|
| KOH pellets, 87.4% purity (Baker) | 30.31 |
| Al(OH)$_3$, 98.5% pellets (Alcoa) | 15.84 |
| H$_2$O, deionized | 75.58 |

The potassium and aluminium sources were mixed with the water which was boiled until a clear solution resulted. The solution was cooled to room temperature and water loss made up.

| Solution B | parts by weight |
|---|---|
| SiO$_2$, Ludox HS40 | 150.24 |
| H$_2$O, deionized | 115.20 |
| Zeolite L seeds, 75 nm, 5.49 wt % solids in water | 1.7884 |

The water was added to the colloidal silica, and the resulting liquids mixed in a blender. The seed suspension was added to the blender contents, and mixed for 30 seconds. Then Solution A was added and mixed for a further 3 minutes, a thickening gel being obtained. The seeds used were obtained as described in Example 1.

The molar composition of the synthesis mixture was:

2.36 $K_2O:Al_2O_3$:10 $SiO_2$:162 $H_2O$ with 252 ppm (0.025%) by weight seeds, based on the total weight of mixture.

326.70 g of synthesis mixture were transferred to a 300 ml stainless steel autoclave, which was placed in an oven at room temperature. The oven was heated over the course of 4 hours to 175° C. and maintained at that temperature for 66 hours.

After cooling, the product was washed 5 times with 750 ml of water, to reach a wash water pH of 9.6. The product was dried at 120° C.; the yield was 50.9 g.

SEM showed a product consisting of cylindrical crystallites with an average length of 0.6 μm, l/d ratio 1.7, with flat basal planes; SEM indicated that the crystal morphology had all the characteristics of a cylindrical KL species. FIGS. 3 and 4 show SE micrographs at magnifications of 10,000 and 40,000 respectively.

EXAMPLE 6 AND COMPARISON EXAMPLE B

In these examples, the effect of colloidal seeds on the product of a synthesis mixture of alkalinity lower than that of Example 5 was examined.

Two synthesis mixtures, both of molar composition:

2.10 $K_2O:Al_2O_3$:10 $SiO_2$:160 $H_2O$ were prepared, that of Example 5 containing in addition 0.075% by weight of seeds produced as described in Example 1, that of Comparison Example B containing no seeds. Both mixtures were hydrothermally treated in stainless steel autoclaves for 80 hours at 150° C.

The product of Example 6 was excellently crystalline and pure zeolite L, while that of Comparison B consisted mainly of zeolite W and amorphous material.

EXAMPLE 7

A synthesis mixture with a molar composition of 3.14 $K_2O$:0.177 $Al_2O_3$:10 $SiO_2$: 159 $H_2O$ was prepared. The $K_2O:Al_2O_3$ ratio of this synthesis mixture was such that if hydrothermally treated on its own a zeolite L heavily contaminated with zeolite T and amorphous material would result. The mixture was, however, seeded with 255 ppm (0.025%) by weight 75 nm KL seed crystals, prepared as described in Example 1.

The mixture was treated for 80 hours at 170° C. in a stainless steel autoclave, washed with water to pH 9.5, and dried at 120° C. The product was pure zeolite KL. SEM showed a product of disk-shaped crystals with flat basal planes ("hockey puck" type crystals). FIGS. 5 and 6 show SE micrographs at magnifications of 10,000 and 40,000 respectively.

EXAMPLE 8

The following two solutions were prepared:

| Solution A | parts by weight |
| --- | --- |
| KOH pellets, 87.3% purity (Baker) | 62.16 |
| Al(OH)$_3$, 98.5% (Alcoa) | 32.47 |
| H$_2$O, deionized | 157.00 |

| Solution B | parts by weight |
| --- | --- |
| SiO$_2$, Ludox HS40 | 308.00 |
| H$_2$O, deionized | 236.21 |
| Colloidal KL seed suspension (75 nm, 5.49 wt. % solids in water) | 3.67 |

The solutions were prepared and mixed as described in Example 5.

The molar composition of the synthesis mixture was:

2.36 $K_2O:Al_2O_3$:10 $SiO_2$:162 $H_2O$ with 253 wt. ppm seeds, based on the total weight of the mixture.

The synthesis mixture was transferred to a 1 liter stirred stainless steel autoclave. The autoclave was heated up over 8 hours to 150° C. with stirring at 80 rpm (tip speed≈0.4 M/S). When the temperature reached≈150° C. the stirring was stopped and the mixture was kept under quiescent conditions for 60 hours at this temperature. The product was washed several times with water to reach a pH of 10.9 and was dried in an oven at 120° C.

XRD showed that the product was excellently crystalline KL without any trace of contaminants such as zeolite W.

SEM showed that the product consisted of very uniform submicron cylindrical crystals with a length of about 0.4 μm and with flat basal planes.

Figure 7:
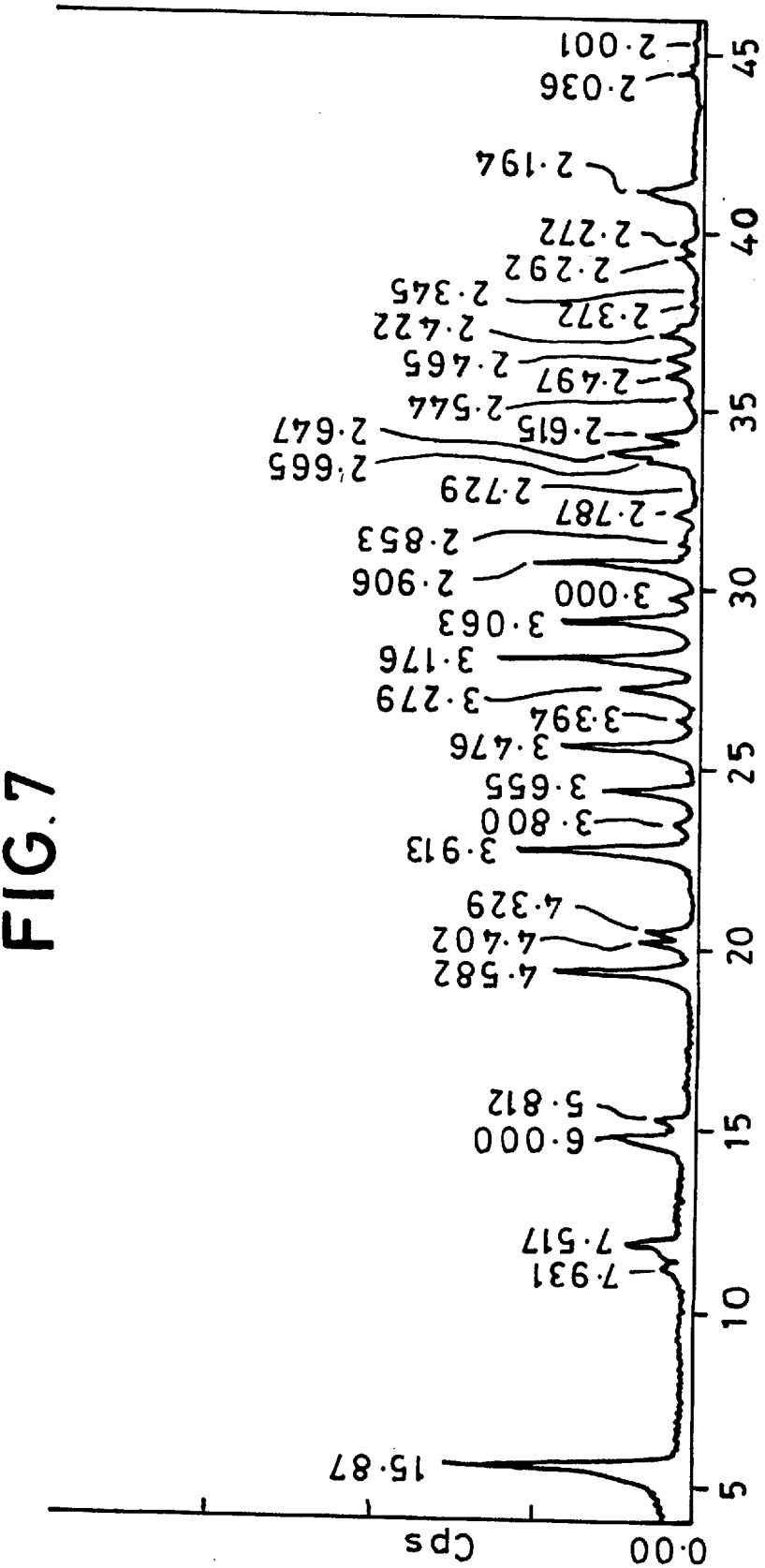
FIG. 7 is an x-ray diffraction pattern of the product of Example 8.

The X-ray diffractogram is given in μm in FIG. 7; SEM micrographs at 10,000X and 40,000X are shown in FIGS. 8 and 9.

COMPARISON EXAMPLE C

This example describes a procedure in accordance with U.S. Pat. No. 5,396,009, making gallium-LTL from a synthesis mixture containing 50 weight ppm of $Mg^{2+}$ species.

Solution A—potassium gallate solution

| Component | No. | Purity | Parts by wt. | Supplier |
| --- | --- | --- | --- | --- |
| KOH pellets | 1 | 87.4% | 33.34 | J. T. Baker |
| Ga$_2$O$_3$ | 2 | 99.999% | 12.18 | Ingal |
| H$_2$O | 3 | deionized | 99.99 | |

Components 1 and 2 were dissolved in 3 with boiling until clear. The solution was cooled down to room temperature. A portion of component 3 (50.00 parts) was used to transfer the potassium gallate solution quantitatively to the silicate solution:

Solution B—silicate solution containing 50 wt. ppm $Mg^{2+}$

| Component | No. | Purity | Parts by wt. | Supplier |
| --- | --- | --- | --- | --- |
| Ludox HS-40 | 1 | 40% SiO$_2$ | 150.29 | Du Pont |
| H$_2$O | 2 | D.I. | 14.06 | |
| Mg$^{2+}$-containing H$_2$O (Mg$^{2+}$-source = Mg (NO$_3$)$_2$ · 6H$_2$O) | 3 | Mg$^{2+}$ content: 0.245 mg/g | 79.49 | |

Components 1, 2 and 3 were mixed in a blender for about 2 minutes. The potassium gallate solution (A) was added to the content of the blender. The two solutions were mixed for about 4 minutes. A slightly blueish but clear non gelating mixture was obtained.

The molar composition of the synthesis mixture was:
2.60 $K_2O$:0.65 $Ga_2O_3$:10 $SiO_2$:160 $H_2O$
The mixture contained 50 wt. ppm $Mg^{2+}$ species.
343.96 parts of the synthesis mixture were transferred to a stainless steel autoclave. The autoclave was placed in an oven at room temperature. The oven was heated up to 150° C. over 1 hour and kept at this temperature for 39 hours.

The product was washed 4 times with 700 parts of water to a pH of 10.4 and was subsequently dried at 120° C. for 16 hours. The weight of product obtained was 38.8 parts.

According to XRD the product was Gallium LTL slightly contaminated with unreacted gel particles as indicated by the presence of a slight "halo" between 2 theta 20 and 35. SEM confirmed the presence of amorphous material and showed that the particles were large: the diameter was between 1.5 and 3 $\mu$m and the length was between 0.7 and 1.0 $\mu$m.

When Al-LTL crystallizes in the presence of trace quantities of divalent cations, e.g., $Mg^{2+}$, the particle size and particle size distribution are very significantly reduced versus the Al-LTL product obtained from the same synthesis mixture not containing divalent cations.

COMPARATIVE EXAMPLE D

The same synthesis mixture as prepared in Example C, but not containing (added) divalent cations and crystallized under the same conditions also gave a large crystal size Ga-LTL contaminated with amorphous material.

Figure 10:
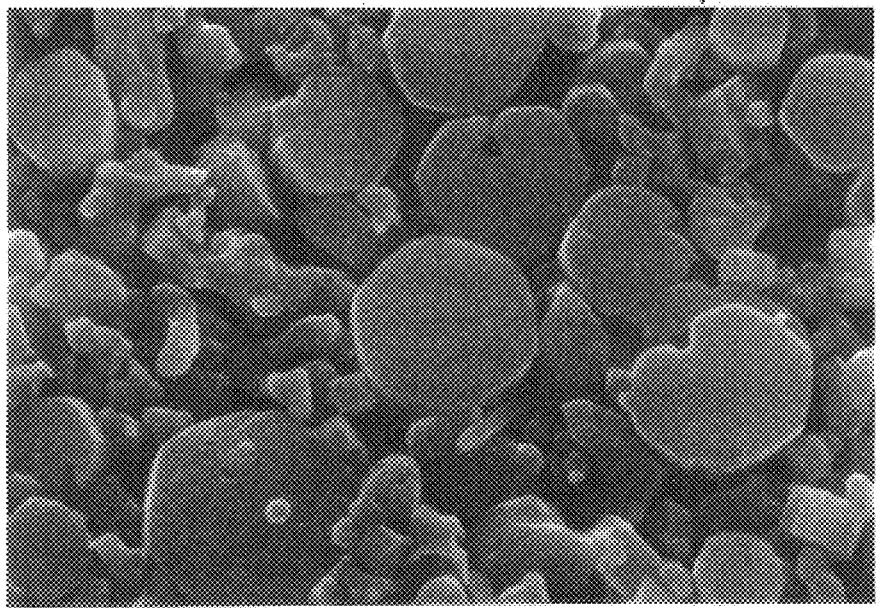
FIGS. 10 and 11 are SEM micrographs of the products obtained in Comparative Examples C and D, respectively.
Figure 11:
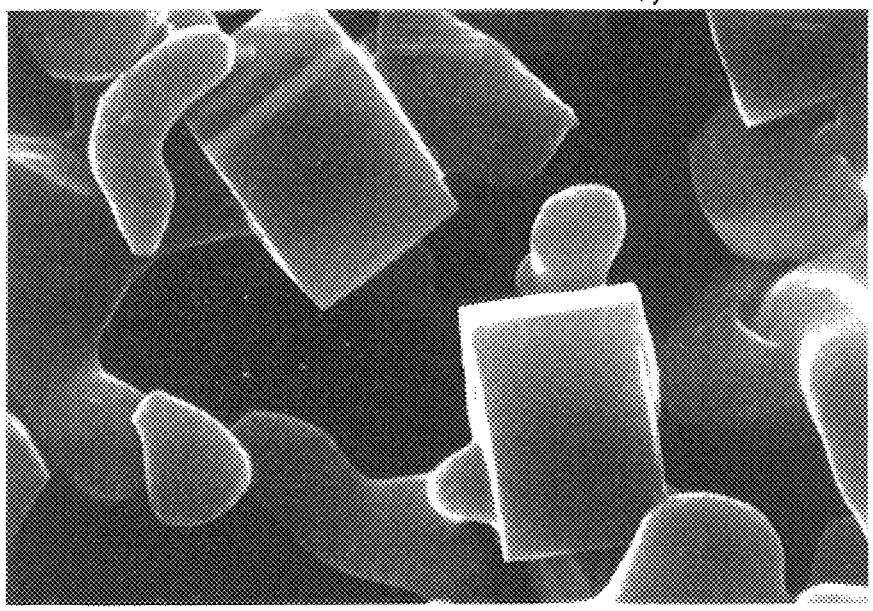

SEM micrographs of the products obtained in Comparisons C and D are shown in FIGS. 10 and 11.

EXAMPLE 9

Synthesis of Ga-LTL in the presence of 50 wt. ppm colloidal LTL seeds.

A synthesis mixture with a molar composition of:
2.60 $K_2O$:0.65 $Ga_2O_3$:10 $SiO_2$:160 $H_2O$ and containing 50 wt. ppm colloidal LTL seeds was prepared using the same procedure as in Comparison Examples C and D. The mixture was crystallized for 39 hours at 150° C. The resulting product was washed several times with water to a pH of 9.6 and was subsequently dried at 120° C. The product yield (parts product/100 parts gel) was 10.1. XRD showed that the product was excellently crystalline and pure and consisted of uniform particles with a length of 0.3–0.5 $\mu$m and a diameter between 0.5–0.8 $\mu$m. The l/d ratio was≈0.6.

EXAMPLE 10

Synthesis of Ga-LTL in the presence of 250 wt. ppm colloidal LTL seeds.

A synthesis mixture with the same molar composition as in Example 9, but containing 250 wt. ppm colloidal seeds, was crystallized in the same way as described in that Example. The resulting product was washed to pH 9.5 and dried at 120° C. The product yield was 10.2. According to XRD the product was excellently crystalline and pure and SEM showed that the product consisted of uniform particles with a length between 0.1 and 0.3 $\mu$m and a diameter between 0.2 and 0.5 $\mu$m. The l/d ratio was≈0.6.

The results of Examples 9 and 10 show that colloidal LTL seeds are extremely effective in the formation of Ga-LTL and to control the particle dimensions by adjusting the seed level.

Figure 12:
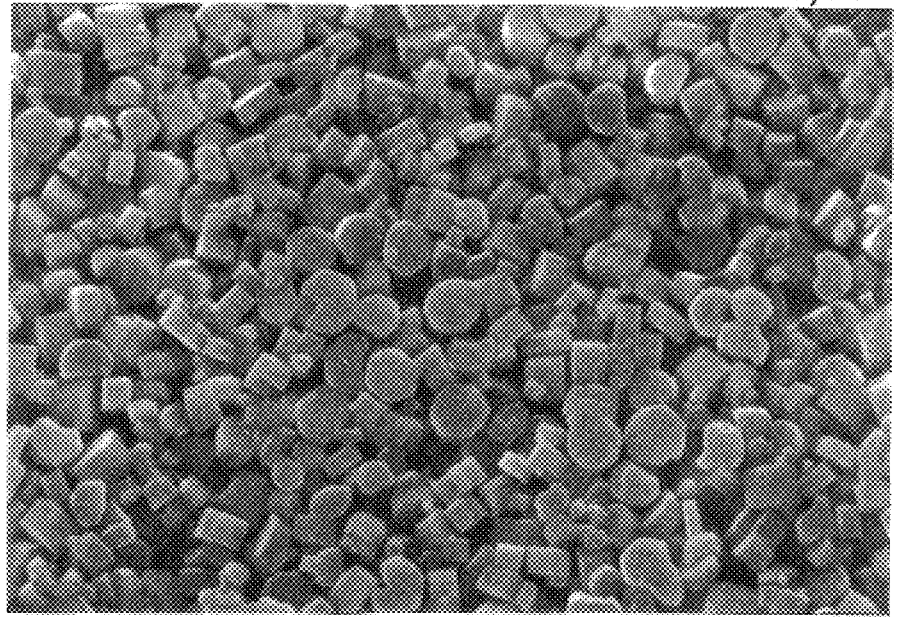
FIGS. 12 and 13 are SEM micrographs of the products obtained in Examples 9 and 10, respectively.
Figure 13:
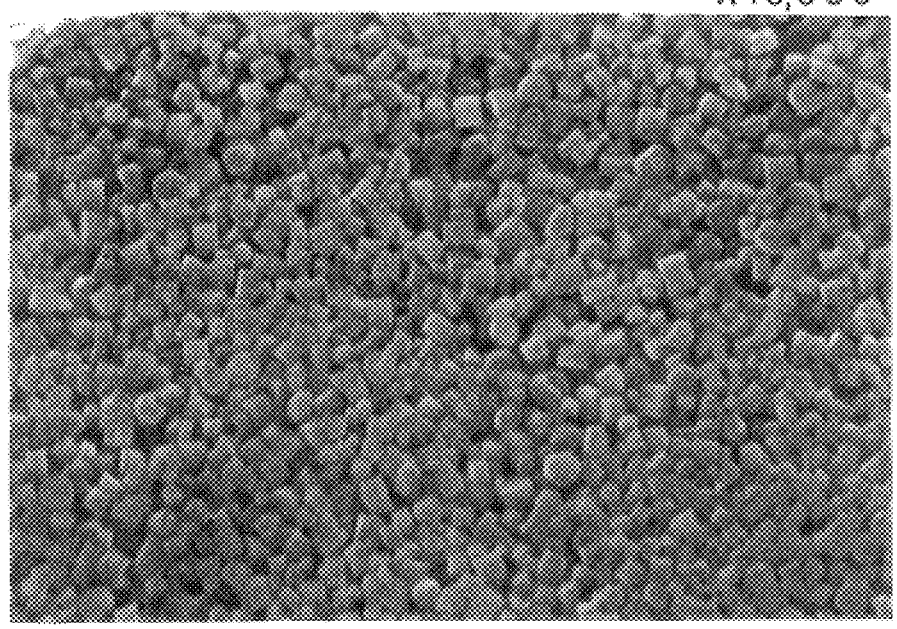
Figure 14:
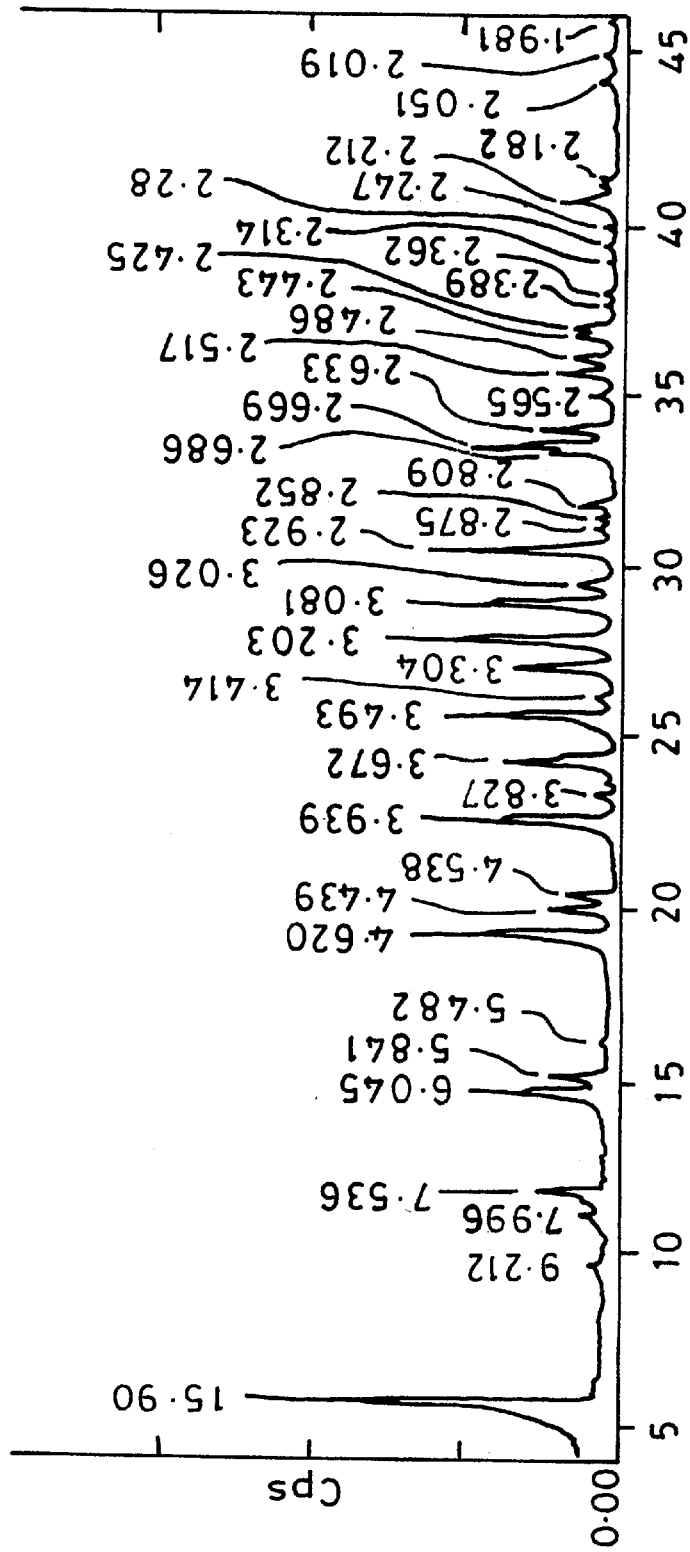
FIG. 14 is an x-ray diffraction pattern of the product obtained in Example 11 from crystallization at 150° C.
Figure 15:
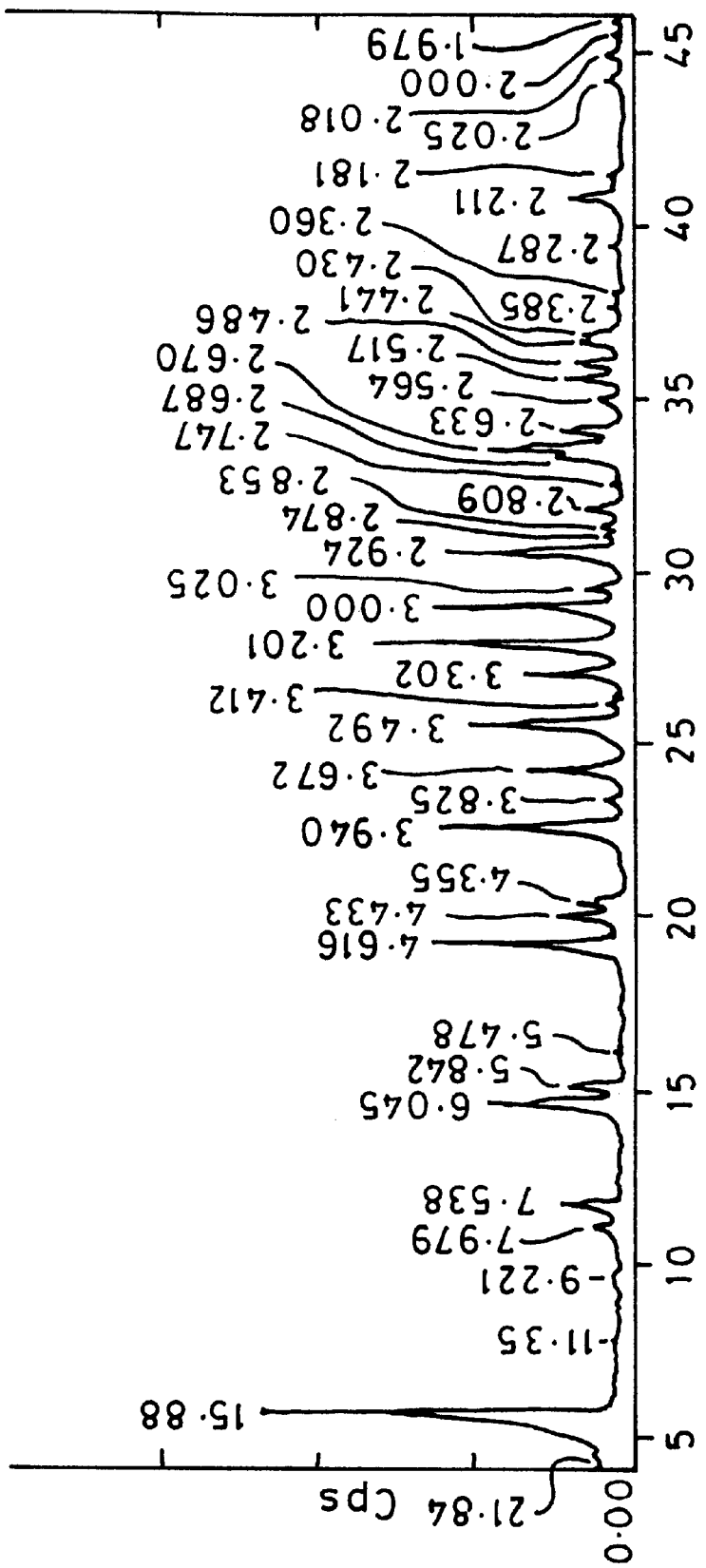
FIG. 15 is an x-ray diffraction pattern of the product obtained in Example 11 from crystallization at 175° C.
Figure 16:
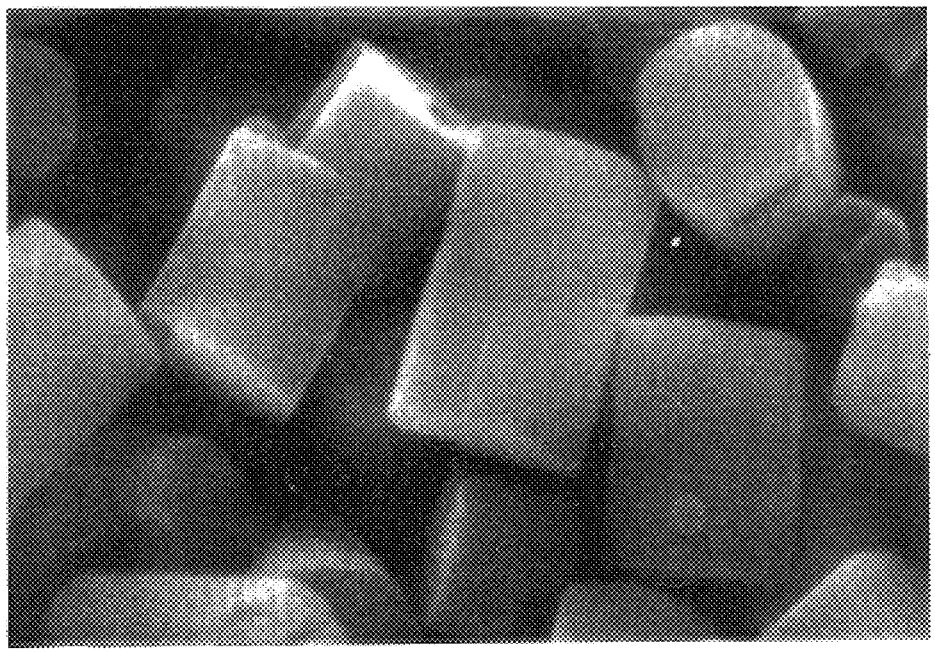
FIG. 16 is an SEM micrograph of the product obtained in Example 11 from crystallization at 150° C.
Figure 17:
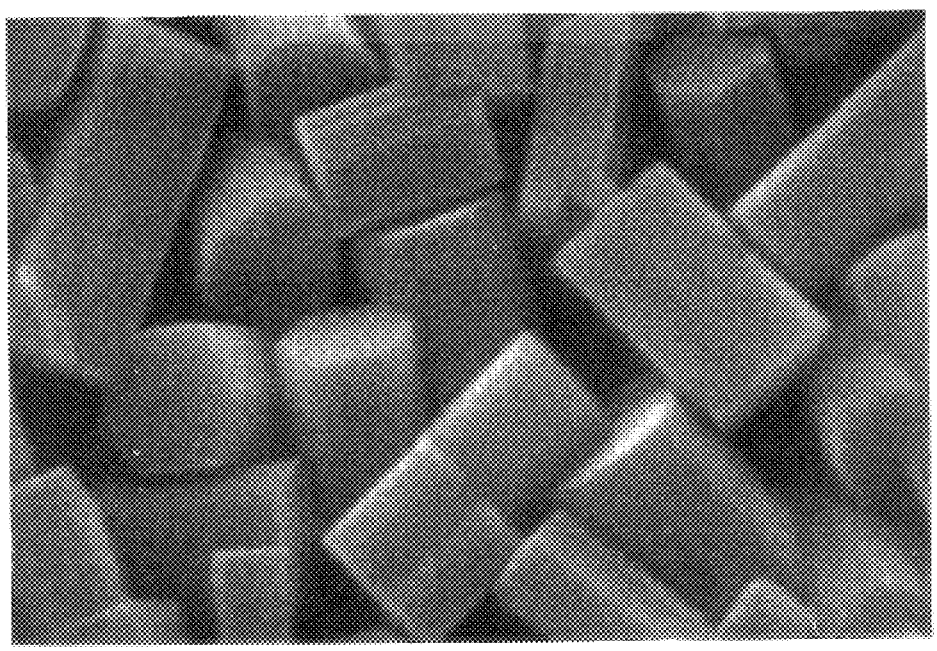
FIG. 17 is an SEM micrograph of the product obtained in Example 11 from crystallization at 175° C.

SEM micrographs of the products obtained in Examples 9 and 10 are given in FIGS. 12 and 13.

EXAMPLE 11

Synthesis of Ga-LTL from a Ga-enriched synthesis mixture in the presence of 75 wt. ppm seeds.

A synthesis mixture was prepared containing 75 wt. ppm colloidal seeds. In this case the $Ga_2O_3$ content of the synthesis mixture was increased by 92% while the alkalinity of the mixture was reduced from $K_2O/SiO_2$=0.26 to $K_2O/SiO_2$=0.24. The molar composition was:

2.40 $K_2O$:1.25 $Ga_2O_3$:10 $SiO_2$:160 $H_2O$

This was done to investigate the "tolerance" of the synthesis to the formation of unwanted zeolite W. The synthesis mixture was divided between two stainless steel autoclaves. One synthesis mixture was aged for 48 hours at 150° C., while the other was aged for 24 hours at 175° C. After washing and drying the product yields were for the 150° C. synthesis 19.6 and for the 175° C. synthesis 19.4. According to XRD and SEM the products were excellently crystalline and pure and had an advanced morphology, i.e., microscopically flat basal planes. X-ray diffractograms and SEM micrographs of both 150° C. and 175° C. products are given in FIGS. 14 to 17.

EXAMPLES 12 to 15

In these four examples, various procedures were adopted in the manufacture of supported zeolite-L containing layers.

For each example, a porous alpha-alumina disk was washed for 10 minutes in n-heptane in an ultrasonic bath, dried for 5 minutes in air, washed for 10 minutes in acetone in the ultrasonic bath and dried in a 50° C. oven for 1 hour. The disks for Examples 12 to 14 were then soaked in water for 2 hours under vacuum, and spun-dried for 30 seconds at 4000 r.p.m. This treatment was omitted for Example 15, the disk being kept at 50° C. until the next stage.

A colloidal suspension of 75 nm zeolite L seeds was applied dropwise to the surface of the disks for Examples 13 to 15. The disks were allowed to stand for 10 seconds with the liquid on the surface and then spun for 30 seconds at 4000 r.p.m. For Examples 13 and 14, the suspension contained 9.56% by weight seeds; for Example 15, the concentration was 0.48% by weight. The seeding step was omitted for Example 12.

Synthesis mixtures of the following compositions by weight were prepared:

| Solution A | Exs. 12, 13 | Exs. 14,15 |
| --- | --- | --- |
| KOH (Baker, 87.4% purity) | 14.47 | 14.50 |
| Al(OH)$_3$ (Alcoa) | 7.90 | 7.89 |
| H$_2$O, deionized | 94.31 | 94.32 |

Solution A was prepared as described in Comparison Example A.

| Solution B | Exs. 12, 13 | Exs. 14,15 |
| --- | --- | --- |
| SiO$_2$ (Ludox HS40) | 75.04 | 75.00 |

In each Example, Solution A was quantitatively mixed with Solution B. In Example 13, mixing took place before disk seeding, and so the mixture had time (about 7 minutes) after being poured into an autoclave to become viscous before the Example 12 and 13 disks were immersed; the gel surface was not completely flat. In Examples 14 and 15, the disks were seeded and made ready before the synthesis mixture was made up so when the disks were immersed, treated face down, in the synthesis mixture in the autoclave the gel was still in a pourable state, its surface was flat, and good contact between the seed layer and the gel was achieved.

In each Example, the autoclave was heated over 2 hours to 175° C. and maintained at that temperature for 24 hours. After allowing the mixture to cool, the autoclave was opened, the supports rinsed with water and washed at 70° C. until the conductivity of the washwater was 5 μ Siemens/cm at 70° C. (in 200 ml water) and the disks dried at 100° C. overnight.

Table 3 below summarizes the differences in the procedures used in Examples 12 to 15.

| Example No. | 12 | 13 | 14 | 15 |
|---|---|---|---|---|
| Vacuum immersion of disk in water | YES | YES | YES | NO |
| Seeding (concentration) | NO | 9.56% | 9.56% | 0.48% |
| Synthesis mixture gelled before disk immersion | YES | YES | NO | NO |

The coated disks were examined by XRD and SEM. XRD showed that in all four cases a layer comprising zeolite L admixed with Zeolite W has grown on the support.

When examined by SEM, the product of Example 12 showed a zeolite layer about 30 μm thick. Zeolite L predominates, consisting of randomly oriented hexagonal crystals with a length between 0.5 and 2.0 μm, l/d ratio about 3. The zeolite W crystals, also randomly oriented throughout the zeolite L layer, are about 30 μm long and 10 μm thick.

SEM analysis of the Example 13 product showed a seed layer of 25 μm thickness on the support, on top of which are deposited first a layer, about 1 to 2 μm thick, of hexagonal Zeolite L crystals, length between 0.5 and 15 μm, l/d ratio about 3, contaminated with Zeolite W crystals, and a second, detachable layer, about 40 μm thick, consisting of large (30 μm×10 μm) zeolite W crystals embedded in a zeolite L matrix.

SEM examination of the Example 14 product did not reveal the seed layer, but a zeolite layer, about 30 μm thick, is formed on a first thin layer (about 2 μm) of zeolite L crystals between 0.5 and 2 μm, l/d ratio about 3, oriented with the c-axis at 60° to 90° to the support surface. The thick zeolite layer is largely zeolite L contaminated with zeolite W.

SEM examination of the Example 15 product shows in a large area of the disk a thin layer of zeolite L crystals (diameter of cross section about 300 nm, l/d ratio about 3) oriented with the c-axis close to 90° to the support surface. (This layer is probably developed from the seed layer, which is not observed.) In some parts of the disk, the layer is overlaid by an easily detachable layer, 30 μm thick, of zeolite L in which large zeolite W crystals are embedded.

When subjected to the dye permeation test, Examples 12 to 14 products readily absorbed rhodamine B. The Example 15 product only absorbed the dye at the edge of the disk, indicating that a densely intergrown zeolite layer was formed.

Figure 18:
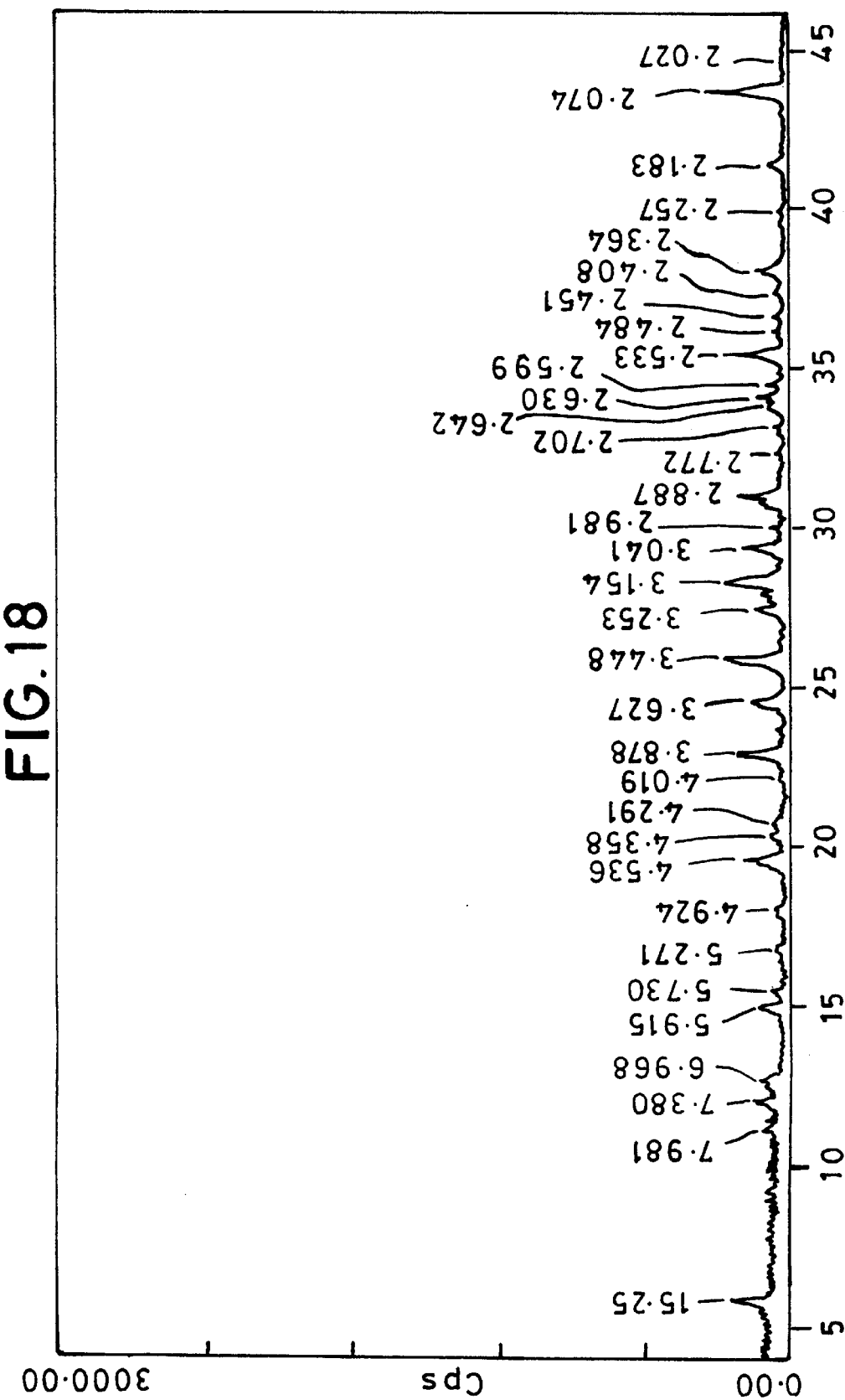
FIGS. 18 and 19 are x-ray diffraction patterns of the products obtained in Examples 14 and 15, respectively.
Figure 19:
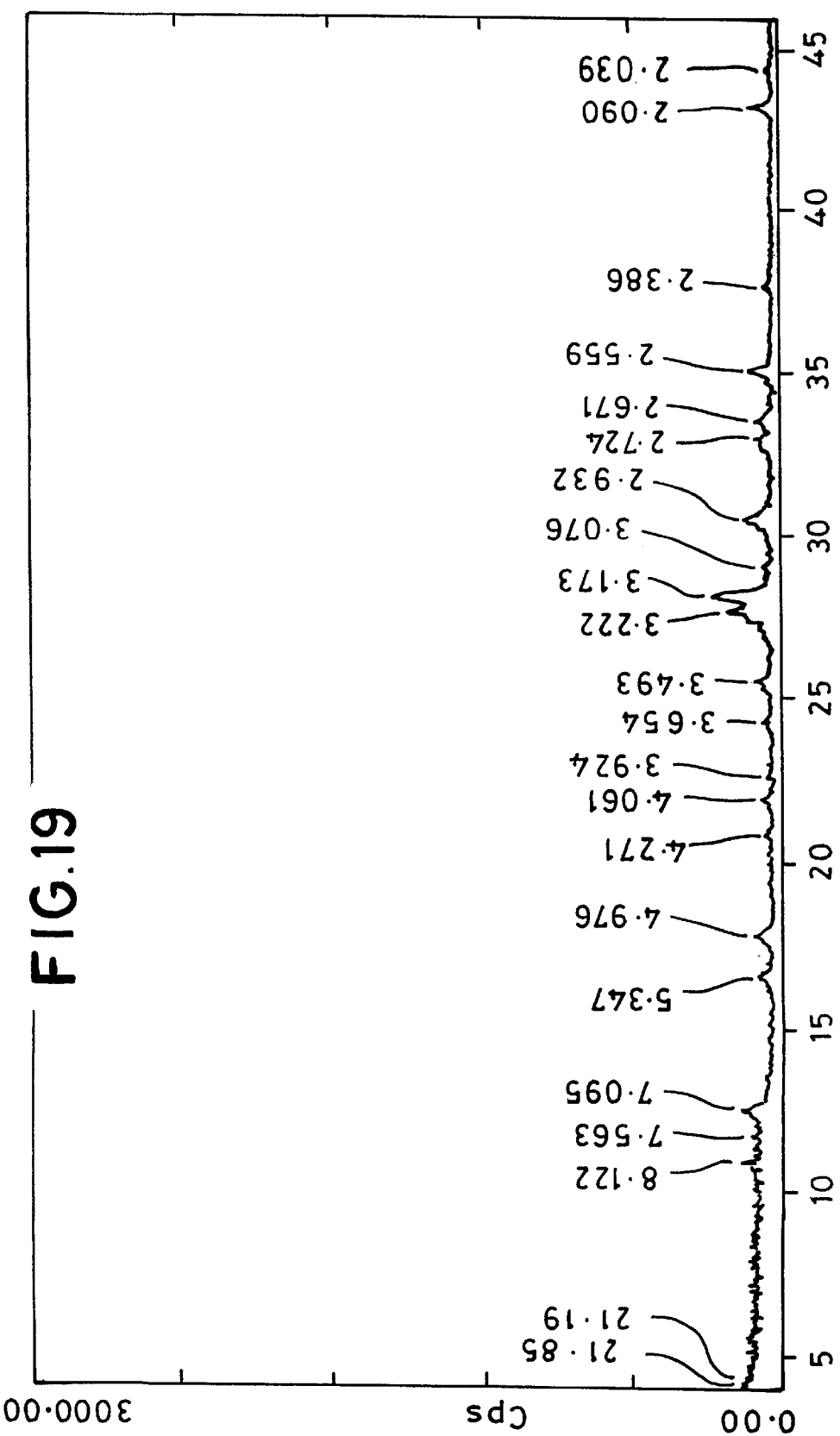

FIGS. 18 and 19 show the XRD patterns of Examples 14 and 15 products.

The synthesis mixture in which the disks are immersed may also contain colloidal zeolite L seeds to reduce or avoid zeolite W formation in the layer.

We claim:

1. A process for the manufacture of a colloidal suspension of an LTL zeolite wherein a synthesis mixture having a composition, given in terms of molar proportions with the solid components being calculated in terms of their oxides, in the ranges:

| | |
|---|---|
| $K_2O:(K_2O + Na_2O)$ | from 0.33 to 1:1 |
| $(K_2O + Na_2O):SiO_2$ | from 0.35 to 0.5:1 |
| $SiO_2:Al_2O_3$ | from 10 to 40:1 |
| solvent free of ammonia: $(K_2O + Na_2O)$ | from 15 to 25:1 | is subjected to thermal treatment at a temperature below 100° C. for a time sufficient to form a colloidal suspension of an LTL zeolite having a particle size of at most 100 nm.

2. A process as claimed in claim 1, wherein the $SiO_2:Al_2O_3$ ratio is within the range of from 10 to 28:1.

3. A process as claimed in claim 1, wherein the $SiO_2:Al_2O_3$ ratio is within the range of from 12 to 28:1.

4. A process as claimed in claim 1, wherein thermal treatment is carried out at a temperature within the range of from 40° to 97° C.

5. A process as claimed in claim 1, wherein thermal treatment is carried out for a time within the range of from 48 to 500 hours.

6. A process as claimed in claim 1, wherein thermal treatment is carried out for a time of at most 84 hours.

7. A process as claimed in claim 1, wherein the solvent is water.

8. A process as claimed in claim 1, wherein the colloidal suspension is washed with water until the wash water has a pH of from 9 to 12, optionally the zeolite is cation exchanged, and optionally calcined.

9. A process as claimed in claim 1, wherein the resulting zeolite has a composition of the Formula $$0.9 \text{ to } 1.3 \text{ } M_2/nO:Al_2O_3:5.2 \text{ to } 6.9 \text{ } SiO_2$$

wherein M represents an exchangeable cation of valence n.

10. A process for the manufacture of an LTL zeolite which comprises forming a synthesis mixture having a composition, given in terms of molar proportions with the solid components calculated in terms of their oxides, in the ranges:

| | |
|---|---|
| $K_2O:(K_2O + Na_2O)$ | from 0.60 to 1:1 |
| $(K_2O + Na_2O):SiO_2$ | from 0.18 to 0.36:1 |
| $SiO_2:Ga_2O_3$ | from 5 to 18:1 |
| solvent:$(K_2O + Na_2O)$ | from 25 to 90:1 | and also containing at least 0.005% by weight seed crystals of an LTL zeolite of particle size at most 100 nm, and subjecting the seed-containing synthesis mixture to a hydrothermal treatment at a temperature and for a time sufficient to form an LTL zeolite.

11. A process as claimed in claim 10, wherein the hydrothermal treatment is carried out at a temperature within the range of 100° C. to 180° C. and for a time within the range of from 4 to 200 hours.

12. A process as claimed in claim 10, wherein from 0.005% to 0.10% by weight of seeds is employed, based on the weight of the synthesis mixture.

13. The process of claim 12 wherein from 0.015% to 0.05% by weight seeds is employed.

14. A process as claimed in claim 10, wherein the seeds have a particle size within the range of 60 to 80 nm.

15. A process as claimed in claim 10, wherein the solvent is water.

16. A process as claimed in claim 10, wherein the resulting zeolite is washed with water until the wash water has a pH of from 9 to 12, optionally, the zeolite is cation exchanged, and optionally calcined.

17. A process as claimed in claim 10, wherein said hydrothermal treatment is carried out with stirring, during heating the synthesis mixture to the hydrothermal treatment temperature.

* * * * *